United States Patent
Zang et al.

(10) Patent No.: US 10,043,990 B2
(45) Date of Patent: Aug. 7, 2018

(54) DUAL-GATE CHEMICAL FIELD EFFECT TRANSISTOR SENSOR

(71) Applicant: University of Utah Research Foundation, Salt Lake City, UT (US)

(72) Inventors: Ling Zang, Salt Lake City, UT (US); Benjamin R. Bunes, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/807,527

(22) Filed: Jul. 23, 2015

(65) Prior Publication Data

US 2017/0110678 A1   Apr. 20, 2017

Related U.S. Application Data (60) Provisional application No. 62/067,332, filed on Oct. 22, 2014, provisional application No. 61/999,369, filed on Jul. 23, 2014.

(51) Int. Cl.
*G01N 27/00* (2006.01)
*H01L 21/336* (2006.01)
(Continued)

(52) U.S. Cl.
CPC ..... *H01L 51/0554* (2013.01); *G01N 27/4141* (2013.01); *H01L 51/001* (2013.01);
(Continued)

(58) Field of Classification Search
CPC ........ G01N 27/00; H01L 21/336; H01L 21/00
(Continued)

(56) References Cited

U.S. PATENT DOCUMENTS 4,499,482 A * 2/1985 Levine ............. H01L 27/14649
                                                    257/290
7,084,442 B2   8/2006 Bertagnolli
(Continued)

OTHER PUBLICATIONS

Wikipedia, "Field-effect transistor", http://en.wikipedia.org/wiki/Field-effect_transistor, as modified on Aug. 25, 2014, 10 pages.
(Continued)

*Primary Examiner* — Brian J. Sines
(74) *Attorney, Agent, or Firm* — Thorpe North & Western, LLP (57) ABSTRACT

A chemical sensing field effect transistor device is disclosed. The device can include a control gate structure interfacing a control side of a semiconductor channel region, a source region, and a drain region. The control gate structure can comprise a control gate dielectric and a control gate electrode. The device can include a sensing gate structure interfacing the semiconductor channel region, the source region, and the drain region at a sensing side of the semiconductor channel region opposite the control gate structure. The sensing gate structure can comprise a sensing gate dielectric, and a sensing gate electrode. The device can include a functional layer interfacing the sensing gate electrode opposite the sensing gate dielectric. The functional layer can have an exposed interface surface. The functional layer can be capable of binding with a target analyte material sufficient to create a measurable change in conductivity across the semiconductor channel region.

16 Claims, 8 Drawing Sheets

(51) Int. Cl.
    *H01L 21/00*      (2006.01)
    *H01L 51/05*      (2006.01)
    *H01L 51/00*      (2006.01)
    *G01N 27/414*     (2006.01)

(52) U.S. Cl.
    CPC ...... *H01L 51/0006* (2013.01); *H01L 51/0022* (2013.01); *H01L 51/0545* (2013.01); *H01L 51/0558* (2013.01); *H01L 51/0053* (2013.01)

(58) Field of Classification Search
    USPC ..... 422/50, 68.1, 82.01, 82.02; 436/43, 149; 438/270, 48, 49
    See application file for complete search history.

(56)        References Cited

U.S. PATENT DOCUMENTS

| | | | |
|---|---|---|---|
| 7,824,530 | B2 | 11/2010 | Yoo et al. |
| 8,735,887 | B2 | 5/2014 | Murai et al. |
| 2004/0056284 | A1 | 3/2004 | Nagaoka |
| 2008/0069971 | A1 | 3/2008 | Keersmaecker |
| 2008/0185616 | A1* | 8/2008 | Johnson ............... G01N 27/129 257/253 |
| 2009/0066347 | A1* | 3/2009 | Uenluebayir .......... G01N 27/12 324/686 |
| 2009/0267057 | A1 | 10/2009 | Sepas |
| 2010/0230731 | A1 | 9/2010 | Armgarth |
| 2011/0169056 | A1 | 7/2011 | Wey |
| 2011/0169057 | A1 | 7/2011 | Tsukada |
| 2011/0239735 | A1 | 10/2011 | Setayesh |
| 2011/0303953 | A1 | 12/2011 | Kamata |
| 2012/0143027 | A1* | 6/2012 | Phillips ............... G01N 27/4145 600/345 |
| 2012/0143568 | A1 | 6/2012 | Kagan |
| 2012/0267693 | A1 | 10/2012 | Holm-Kennedy |
| 2012/0286803 | A1 | 11/2012 | Nackaerts et al. |
| 2013/0115136 | A1 | 5/2013 | Katz |
| 2013/0119440 | A1 | 5/2013 | Ackerson |
| 2013/0200438 | A1 | 8/2013 | Liu et al. |
| 2013/0313569 | A1 | 11/2013 | Usagawa |
| 2014/0021516 | A1 | 1/2014 | Ackerson |
| 2014/0234981 | A1 | 8/2014 | Zarkesh-Ha |
| 2015/0017740 | A1* | 1/2015 | Shalev ............... G01N 27/4146 436/501 |
| 2016/0041155 | A1* | 2/2016 | Takulapalli ........ G01N 27/4145 506/16 |
| 2016/0131613 | A1* | 5/2016 | Jayant .................. C12Q 1/6869 506/9 |
| 2017/0067890 | A1* | 3/2017 | Lin ..................... H01L 51/0093 |
| 2017/0227533 | A1* | 8/2017 | Lin ..................... G01N 33/5438 |

OTHER PUBLICATIONS

Wilson et al, "Chemical Sensors for Portable, Handheld Field Instruments", IEEE Sensors Journal, vol. 1, No. 4, p. 256-274, Dec. 2001.

* cited by examiner

Prior Art
FIG. 1

Prior Art

FIG. 2

Prior Art

DUAL-GATE CHEMICAL FIELD EFFECT TRANSISTOR SENSOR

RELATED APPLICATIONS

This application claims priority to U.S. Provisional Application No. 62/067,332, filed Oct. 22, 2014 and U.S. Provisional Application No. 61/999,369, filed Jul. 23, 2014, each of which are incorporated by reference.

GOVERNMENT INTEREST

This invention was made with government support under U.S. National Science Foundation Grant No. DGE0903715, U.S. National Aeronautics and Space Administration Grant No. NNX12AM67H, and U.S. Department of Homeland Security Grant No. 2009-ST-108-LR0005. The government has certain rights in the invention.

FIELD OF THE INVENTION

This invention relates to the field of chemical field effect transistors including sensors designed to detect adsorbed vapor analytes. Accordingly, the invention involves the fields of electrical engineering, semiconductor physics, materials science and nanotechnology.

BACKGROUND

Detection of chemical species in gas or vapor phases is a rapidly growing field. Toxic chemicals, such as hydrogen cyanide and nitrogen dioxide, are released during combustion or pyrolysis. If not properly exhausted, these chemicals can accumulate, eventually reaching dangerous levels. Other chemicals, such as acetone and various exhaled biomarkers, can be indicators of certain diseases if present in unusual quantities in a person's breath. Chemical detection can also be used as a warning system for potential threats from chemical, biological, and energetic (i.e., explosives) weapons. Furthermore, chemical detection can be used to alleviate the growing concern of air quality in large buildings, where chemicals can accumulate within confined spaces of the buildings.

SUMMARY

A chemical sensing field effect transistor device can comprise a semiconductor channel region interfacing a drain region and a source region. The chemical sensing field effect transistor device can comprise a control gate structure interfacing a control side of the semiconductor channel region, the source region, and the drain region. The control gate structure can comprise a control gate dielectric and a control gate electrode. The chemical sensing field effect transistor device can comprise a sensing gate structure interfacing the semiconductor channel region, the source region, and the drain region at a sensing side of the semiconductor channel region opposite the control gate structure. The sensing gate structure can comprise a sensing gate dielectric, and a sensing gate electrode. The chemical sensing field effect transistor device can comprise a functional layer interfacing the sensing gate electrode opposite the sensing gate dielectric. The functional layer can have an exposed interface surface. The functional layer can be capable of binding with a target analyte material sufficient to create a measurable change in conductivity across the semiconductor channel region.

In one embodiment, the control gate dielectric can be oriented between the semiconductor channel and the control gate electrode. The sensing gate dielectric can be oriented between the semiconductor channel and the sensing gate electrode. The semiconductor channel region can be an organic semiconductor.

The semiconductor channel region can be formed of a semiconducting material such as, but not limited to, organic semiconductor and inorganic semiconductors. In one aspect, the semiconductor channel region can include at least one of: polythiophenes, polynaphthalyene, polyphenylenevinylene, parylenediimides, oligothiophenes, phalocyanines, pentacene, benzodithiophene, carbonyl-bridged bithiazole, and alkyl substituted dioxocyclopenta[b]thiophene. In one optional aspect, the semiconductor channel region can be a hybrid graphene/organic semiconductor. Other suitable semiconductor materials can include, but are not limited to, graphene, carbon nanotubes, semiconducting oxides (e.g. $TiO_2$, $In_2O_3$, etc), semiconducting selenides (e.g. PbSe), semiconducting sulfides (e.g. $MoS_2$), and the like. The semiconductor channel region can be an inorganic semiconductor including at least one material from the semiconductor materials categorized by the periodic table of elements as group IV, III-V, II-VI, I-$VI_2$, or $I_2$-II-IV-$VI_4$.

A surface area of the functional layer can be substantially greater than an interface area between the semiconductor channel region and the sensing gate dielectric. In one aspect, the direction of a flow of current through the semiconductor channel region can be substantially parallel to a plane of the functional layer. In another embodiment, a flow of current through the semiconductor channel region can be substantially orthogonal to the plane of the functional layer, although other configurations may be suitable.

The sensing gate dielectric and the control gate dielectric can comprise an electrical insulator. In one aspect, the dielectric can be at least one of: silicon dioxide, polymethylmethacrylate (PMMA), parylene-c, polyimide, polystyrene, bisdichlorosilylethane, bisdichlorosilylhexane, polyisobultylene, alumina, and hafnium oxide. However, other insulators can also be used such as, but not limited to, vacuum gaps, air gaps, and the like.

In another aspect, the electrodes can comprise at least one of the materials selected from the group consisting of heavily doped inorganic semiconductors, conductive polymers, graphene, conductive composites, metals, ionic gels/liquids, and combinations thereof. The functional layer can comprise at least one member selected from the group consisting of perylene imides, porphyrins and phthalocyanines, carbazoles, anilines, thiophenes, pyrroles, ketones, carbon nanotubes, metal oxides, derivatives thereof, and combinations thereof, the functional layer material being chosen according to a level of adsorptive interaction with a target analyte material. As a general guideline, the functional layer can be from 1 nanometer (nm) to 10 micrometers (µm) in thickness. The functional layer can also include a microstructured or a nano-structured surface to morphologically facilitate target analyte adsorption.

A method of fabricating a chemical sensing field effect transistor device is disclosed. The method can comprise forming a semiconductor channel region interfacing a source region and a drain region. The method can comprise forming a control gate structure interfacing a control side of the semiconductor channel region, the source region, and the drain region. The control gate structure can comprise a control gate dielectric and a control gate electrode. The method can comprise forming a sensing gate structure interfacing the semiconductor channel region, the source region, and the drain region at a sensing side of the semiconductor channel region opposite the control gate. The sensing gate structure can comprise a sensing gate dielectric and a sensing gate electrode. The method can comprise forming a functional layer interfacing the sensing gate electrode. The functional layer can have an exposed interface. The functional layer can be capable of binding with a target analyte material sufficient to create a measurable change in conductivity across the semiconductor channel region.

The semiconductor channel can be an organic semiconductor and is formed using at least one of: solution-processed deposition, electropolymerization, vacuum evaporation and the Langmuir Blodgett technique. The source region and the drain region can optionally be formed from the organic semiconductor according to at least one of: an oxidation-reduction process, ion implantation, chemical doping and electrochemical doping. The source region and the drain region can be formed by depositing conductive materials to form an interface with the organic semiconductor channel. In one aspect, the source and drain regions can be formed, followed by formation or deposition of semiconductor. The semiconductor channel, the source region, and the drain region can also be formed from a substrate comprised of an inorganic material including at least one of the semiconductor materials categorized by the periodic table of elements as group IV, III-V, II-VI, I-VI$_2$, or I$_2$-II-IV-VI$_4$ and are optionally doped with one or more types of charge donors and acceptors.

The sensing gate dielectric and the control gate dielectric can be formed using at least one of: thermal oxidation, chemical vapor deposition, physical vapor deposition, and solution-based deposition. The sensing gate electrode and the control gate electrode can be formed using at least one of: epitaxy, evaporation, vacuum deposition, chemical vapor deposition, atomic layer deposition, physical vapor deposition, or inkjet printing. The functional layer can be formed using at least one of: chemical vapor deposition, physical vapor deposition, solution-based deposition, electrospinning, and electrospraying.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

It should be noted that the figures are merely exemplary of several embodiments of the present invention and no limitations on the scope of the present invention are intended thereby. Further, the figures are generally not drawn to scale, but are drafted for purposes of convenience and clarity in illustrating various aspects of the invention.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used. The singular forms "a," "an," and "the" include plural references unless the context clearly dictates otherwise. Thus, for example, reference to "a gate" includes reference to one or more of such structures, "an analyte" includes reference to one or more of such materials, and "a depositing step" refers to one or more of such steps.

As used herein, "solution-processed deposition" refers to spin-on deposition also known as spin coating wherein a liquid solution is applied to a solid substrate. The wetted substrate is rapidly spun and centrifugal forces evenly distribute the liquid in a thin film across the substrate surface. Solution-processed deposition is often followed by a thermal step in which solvent is evaporated from the film and interactions occur between precursors from the applied solution and the surface of the substrate.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, and sub-ranges such as 10 to 50, 20 to 100, etc.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

The present technology provides a low cost, selective, sensitive field effect transistor (FET) vapor analyte sensor which detects chemical species in their gas or vapor phase. In one configuration, the FET sensor can be a dual gate (DG) chemically-sensing field effect transistor (chemFET), or DG-FET. The DG-FET sensor can integrate with widely used electrical components by taking advantage of the functional materials selectivity. The DG-FET sensor can interface the channel with not one, but two gate structures to reduce threshold voltage, while at the same time maximizing sensitivity by introducing a functional layer engineered to preferentially adsorb target analytes. With respect to the novel sensor design of the DG-FET sensor, organic materials that provide high selectivity and sensitivity as chemiresistors can be used as the functional layer on a sensing gate, minimizing false positives. Furthermore, the generalized structure of the DG-FET sensor can enable a variety of applications, wherein the only component that changes is the functional layer. A control gate can increase the signal over four orders of magnitude, to the microampere range. These relatively high currents can provide compatibility with off-the-shelf electronics, reducing the cost of the supporting circuitry. Finally, the DG-FET sensor can be produced using existing manufacturing techniques. The production processes can use spin coating and thermal evaporation, which are already in use on assembly lines worldwide. There is minimal risk in adapting the manufacturing processes from laboratory to production scale. Compared to all other gas/vapor sensing technologies, the DG-FET sensor described herein is the best combination of cost, sensitivity, selectivity, and manufacturability for widespread applications.

Previous technologies do not function to monitor chemicals of interest at pertinent concentrations. Various detection techniques have been previously investigated for vapor phase analyte detection applications. Many approaches, such as ion mobility spectrometry (IMS) and mass spectroscopy (MS), are prohibitively expensive. Electrochemical cells are a less expensive technique, representing the most widespread means of airborne chemical detection. However, electrochemical cells are not adequately sensitive. For hazard monitoring, detection limits of electrochemical cells are generally at the Occupational Safety and Health Administration (OSHA) standard, and those affected are not warned until the chemical reaches a dangerous level.

Chemiresistors represent another tool for vapor phase analyte detection in previous techniques. However, chemiresistors have drawbacks dependent on the materials used. For example, chemiresistors that are based on metal oxides or carbon allotropes operate at high temperatures and can have issues with selectivity, leading to frequent false positives. Chemiresistors based on polymer swelling can operate at room temperature, but have poor selectivity. In previous techniques, organic semiconductors can be used with great sensitivity and selectivity because their structures are tailored specifically to the chemical of interest. Organic semiconductors comprise highly selective chemiresistive sensors, but adequate conductivity is difficult to achieve because of their intrinsically low charge carrier mobility. The low conductivity also complicates integration of organic semiconductors into electronic circuits, which adds cost and development time.

Figure 1:
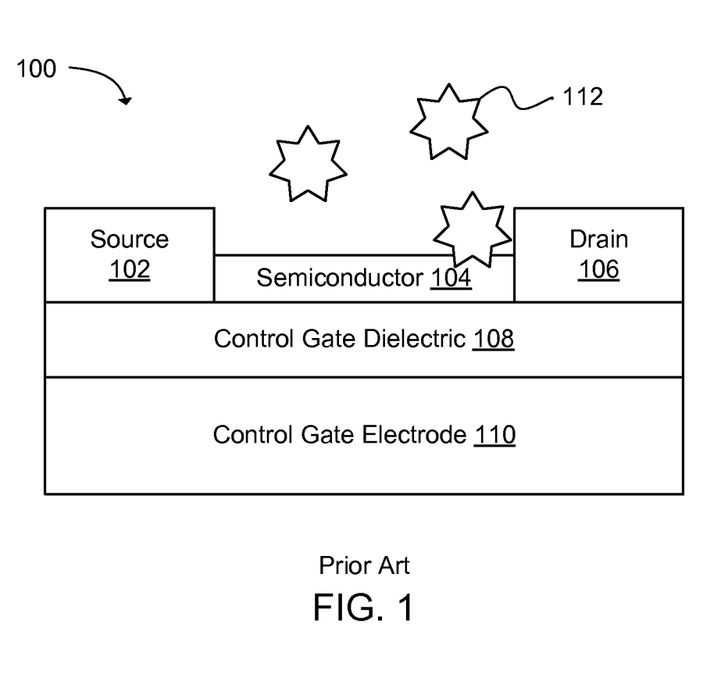
FIG. 1 illustrates a sensing semiconductor (SS) chemical-sensing field effect transistor (chemFET) in accordance with the prior art.

FIG. 1 illustrates a sensing semiconductor (SS) chemical-sensing field effect transistor (chemFET) 100 operable to detect chemical species 112 in accordance with the prior art. The chemical species 112 can be detected when in gas or vapor form. The SS chemFET 100 can also be referred to as SS-FET 100. Field effect transistors can be used for chemical detection can be used to take advantage of the selectivity of organic semiconductors. Field effect transistors can induce conductivity in otherwise resistive materials by accumulating charge carriers with an electric field.

In early chemFET devices, the SS-FET 100 includes a source 102 and a drain 106. In addition, the SS-FET 100 includes a control gate dielectric 108, a control gate electrode 110 and a semiconductor 104. The control gate dielectric 108 and the control gate electrode 110 are below the semiconductor 104, wherein the semiconductor 104 can be exposed to the atmosphere. The semiconductor 104 can be responsible for both conduction and sensing. While the SS-FET 100 can demonstrate high sensitivity, down to parts per trillion, selectivity can be exceptionally poor. Relative to a chemiresistor, there are more phenomena that can elicit a response from a chemFET. While chemiresistors rely on charge transfer, the SS-FET 100 can also be triggered by the introduction of trap states or swelling if a species in the atmosphere is soluble. The variety of sensing mechanisms can reduce selectivity of the SS-FET 100 to below acceptable levels. In addition, the material constraints required to have both sensitivity and conductivity can be restrictive.

Figure 2:
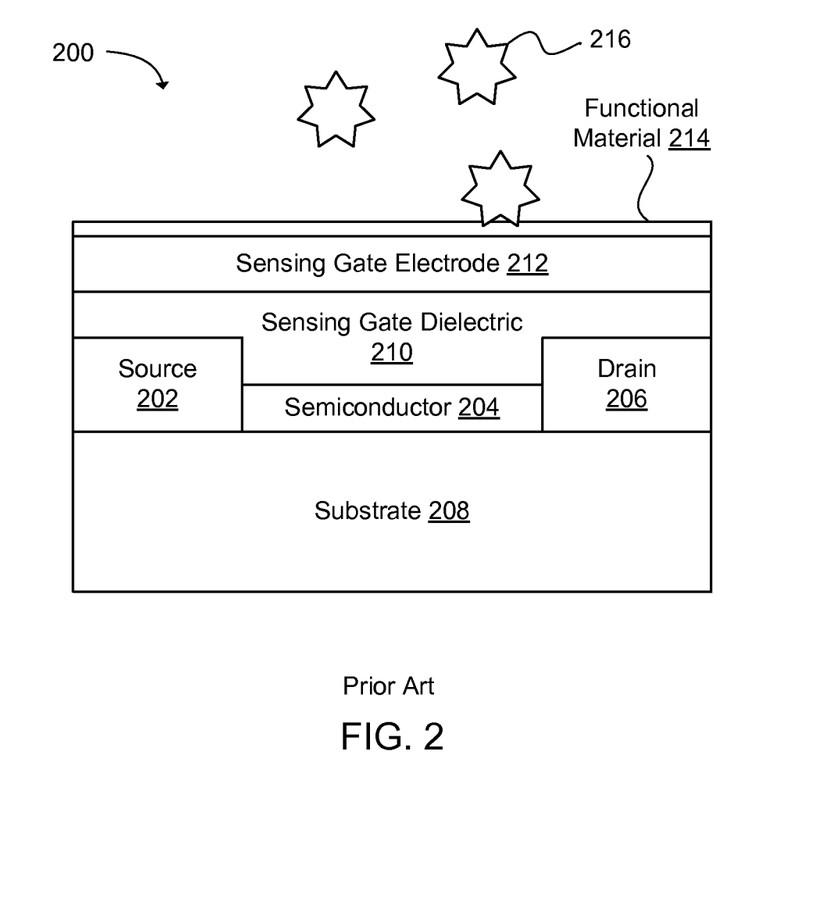
FIG. 2 illustrates a sensing gate (SG) chemical-sensing field effect transistor (chemFET) in accordance with the prior art.

FIG. 2 illustrates a sensing gate (SG) chemical-sensing field effect transistor (chemFET) 200 operable to detect chemical species 216 in accordance with the prior art. The chemical species 216 can be detected when in gas or vapor form. The SG chemFET 200 can also be referred to as SG-FET 200. The SG-FET 200 can provide improved selectivity in comparison to the SS-FET. The SG-FET 200 can include a source 202 and a drain 206. In addition, the SG-FET 200 can include a sensing gate electrode 212, a sensing gate dielectric 210, a semiconductor 204 and a substrate 208. In this configuration, the semiconductor 204 can be buried and the sensing gate electrode 212 can be responsible for interacting with the chemical species 216. The SG-FET 200 can include a functional material 214 that is applied to the sensing gate electrode 212 in order to improve selectivity. In the SG-FET 200, selectivity can be greatly improved since the only detection mechanism is charge transfer. Selectivity is further improved by the wider range of functional materials that can be used, since the sensing material does not need to be conductive in this configuration.

Figure 3:
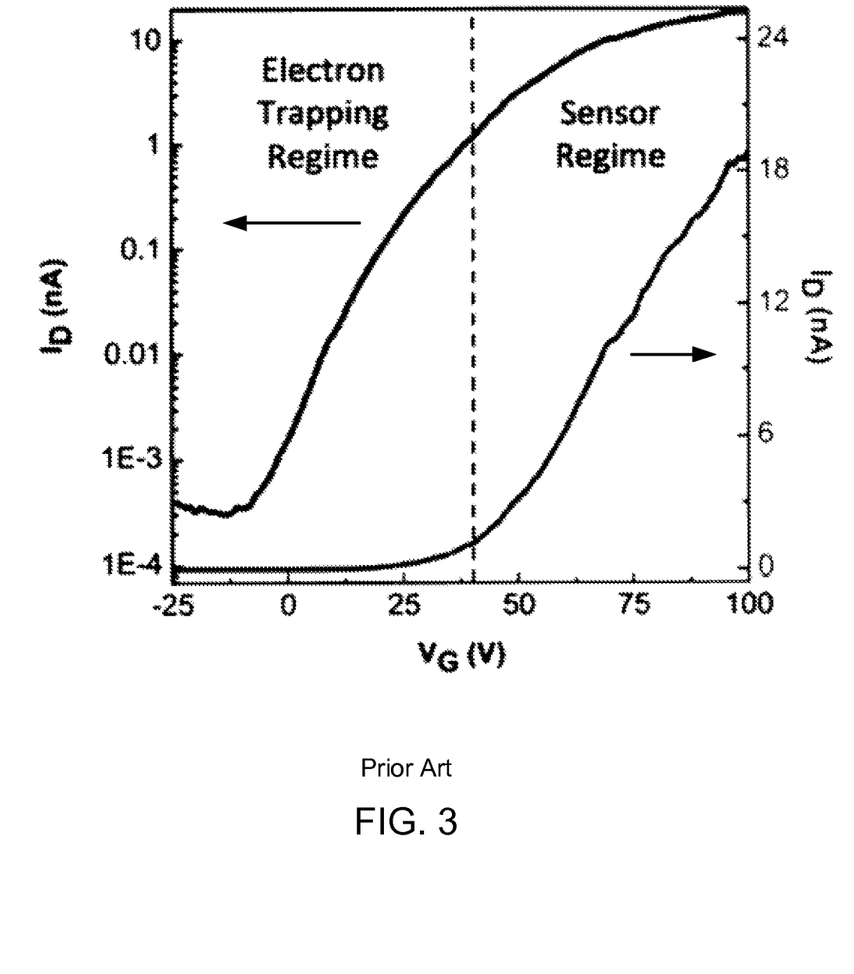
FIG. 3 is a plot of drain current as a function of gate voltage representing a typical performance of a sensing gate (SG) chemical-sensing field effect transistor (chemFET) that includes a high threshold voltage and low sensitivity in accordance with the prior art.

FIG. 3 is a plot of drain current with respect to gate voltage representing a typical performance of a sensing gate (SG) chemical-sensing field effect transistor (chemFET), or SG-FET, that includes a high threshold voltage and low sensitivity. Advances in selectivity for the SG-FET, in comparison to the SS-FET, can come at the expense of sensitivity. The organic semiconductors typically used in SG-FET sensors are vulnerable to trap charge states that cause large threshold voltages, as shown in FIG. 3. These threshold voltages have to be overcome before a measurable current exists. From a sensitivity standpoint, this entails a large accumulation of chemical molecules to satisfy trap charges before a signal can be observed.

Figure 4:
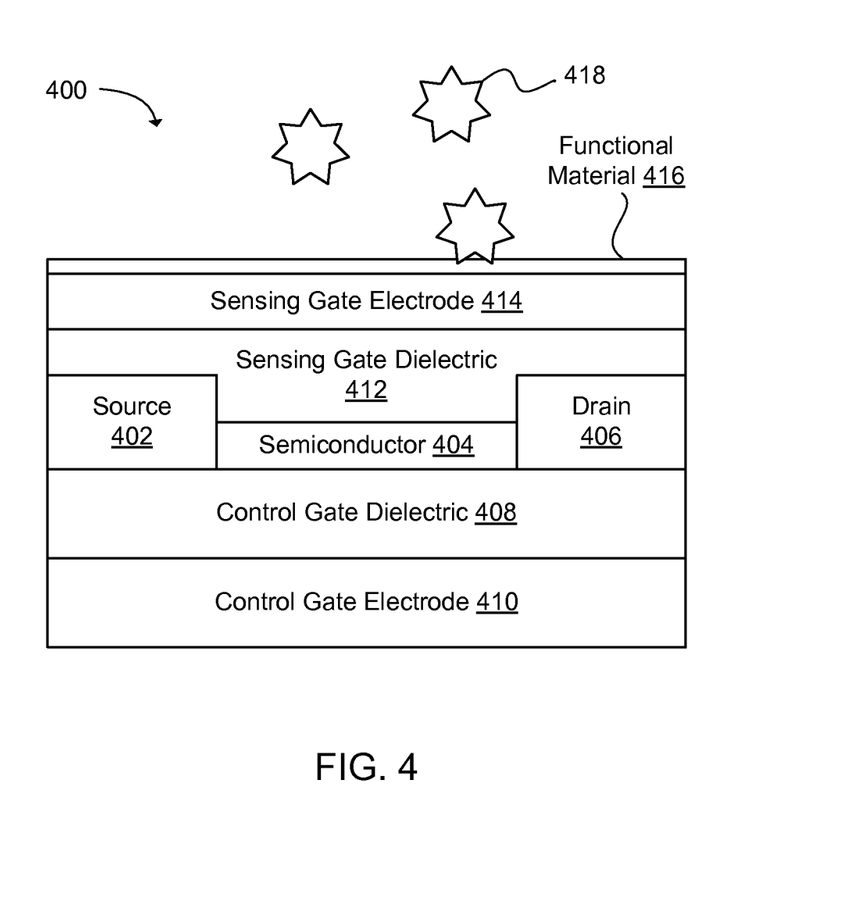
FIG. 4 illustrates a dual gate (DG) chemical-sensing field effect transistor (chemFET) in accordance with one example of the present invention.

FIG. 4 illustrates an exemplary dual gate (DG) chemical-sensing field effect transistor (chemFET) 400 operable to detect chemical species 418. The chemical species 418 can be detected when in gas or vapor form. The DG chemFET 400 can also be referred to as DG-FET 400 and can include a source 402 and a drain 406. In addition, the DG-FET 400 can include a sensing gate electrode 414, a sensing gate dielectric 412, a semiconductor 404, a control gate dielectric 408 and a control gate electrode 410. The DG-FET 400 can be operationally similar to the SG-FET, as previously described, in that the conductivity and sensing are provided by two different materials. Charge transfer at a functionalized sensing gate produces a change in conductivity in the semiconductor 404. However, a second gate (i.e., a control gate) is added to the opposite side of the semiconductor 404. This control gate is used to modulate a threshold voltage, which greatly enhances the sensitivity. Therefore, a sensing gate can be on a first side of the semiconductor 404 and the control gate can be on a second side of the semiconductor 404, wherein the first side and the second side are opposite from each other. The addition of the second gate can enable the use of practical applications for chemically-sensing FETs.

In this configuration, the semiconductor 404 can be buried and the sensing gate electrode 414 can be responsible for interacting with the chemical species 418. The DG-FET 400 can optionally include a functional material 416 that is applied to the sensing gate electrode 414 in order to improve selectivity. In the SG-FET 200, selectivity can be greatly improved since the only detection mechanism is charge transfer. Selectivity is further improved by the wider range of functional materials that can be used, since the sensing material does not need to be conductive in this configuration.

As a non-limiting example, a functional material of perelyne diimide can correspond to target analyte species of amines, nitros, peroxides, chemical warfare agents (CWAs). Perylene imide can be applicable to narcotics, explosives, medical, building health, air quality, defense, etc. As another non-limiting example, the functional materials of porphyrins and phthalocyanines can correspond to target analyte species of peroxides, cyanides, nitros, toxic gases, etc. Porphyrins and phthalocyanines can be applicable to building health, air quality, explosives, health and safety, etc. As another non-limiting example, the functional material of carbazole can correspond to target analyte species of nitros. Carbazoles can be applicable to air quality, explosives, etc. As another non-limiting example, the functional material of aniline can correspond to target analyte species of amines, aldehydes, acids, other volatile organic compounds (VOCs), etc. Anilines can be applicable to narcotics, medical, building health, health and safety, air quality, etc. As another non-limiting example, the functional material of thiophene can correspond to target analyte species of acids, cyanides, nitros, CWAs, other VOCs, etc. Thiophenes can be applicable to health and safety, air quality, explosives, defense, building health, etc. As another non-limiting example, the functional material of pyrrole can correspond to target analyte species of acids, amines, toxic gases, other VOCs, etc. Pyrroles can be applicable to health and safety, narcotics, health, building health, air quality, etc. As another non-limiting example, the functional material of ketone can correspond to target analyte species of acids, amines, etc. Ketones can be applicable to health and safety.

Therefore, SS-FETs generally provide sensitivity, but not selectivity; SG-FETs generally provide selectivity, but not sensitivity; and DG-FETs provide both sensitivity and selectivity. The DG-FET 400 combines the advantageous selectivity and wide range of functional materials of the SG-FET along with the high sensitivity of the SS-FET. The selectivity of the FET sensor can impact the number of chemical species that can be selected for detection (i.e., greater selectivity can result in a more versatile chemically-sensing FET sensor), whereas the sensitivity of the FET sensor can impact whether or not chemical species are detected (i.e., greater sensitivity can result in detection of chemical species of a reduced quantity).

In one configuration, the DG-FET can include a semiconductor channel region interfacing a drain electrode and a source electrode. Additional interfaces of the semiconductor channel, source, and drain regions can comprise a control side and a sensing side. A control gate structure can interface the control side and a sensing gate structure can interface the sensing gate side. The control gate structure can include a control gate dielectric and a control gate electrode where the control gate dielectric is oriented between the semiconductor channel and the control gate electrode. The sensing gate structure can comprise a sensing gate dielectric and a sensing gate electrode where the sensing gate dielectric is oriented between the semiconductor channel and the sensing gate electrode.

The functional layer can interface the sensing gate electrode opposite the sensing gate dielectric. Generally, the functional layer can have an exposed interface surface capable of binding with a target analyte material sufficient to create a measurable change in conductivity across the semiconductor channel region. The semiconductor channel region can be an organic semiconductor including at least one of the following materials: polythiophenes, polynaphthalyene, polyphenylenevinylene, and other conjugated polymers, parylenediimides, oligothiophenes, phalocyanines, pentacene, benzodithiophene, carbonyl-bridged bithiazole, alkyl substituted dioxocyclopenta[b]thiophene, anthracene, rubrene, napthalenediimides, polytriarylamines, oligoarylamines, polythienylenevinylene, and the like. In one aspect, the organic semiconductor can be polythiophenes, polynaphthalyene, polyphenylenevinylene, and other conjugated polymers. In addition, an area of the exposed surface of the functional layer can be substantially greater than an interface area between the semiconductor channel region and the sensing gate electrode.

In one example, the functional layer can include perylene imides, perylene diimide derivatives, porphyrins and phthalocyanines, carbazoles, anilines, thiophenes, pyrroles, ketones, carbon nanotubes, metal oxides, derivatives thereof, and the like. The functional layer can be formed of a material being chosen according to its adsorptive interaction with a target analyte material. The functional layer can also have a micro-structured or nano-structured surface to morphologically facilitate analyte adsorption. Thickness of the functional layer can affect performance and sensitivity. As a general guideline, the functional layer can be from 1 nm to 10 μm in thickness.

In one example, the direction of current through the semiconductor channel region can be substantially parallel to a plane of the functional layer. In another example, the flow of current through the semiconductor channel region is substantially orthogonal to the plane of the functional layer, although other configurations may be suitable (e.g., microrod, nanorods, nanopyramids, etc).

In one example, the sensing and control gate dielectric materials can be comprised of: silicon dioxide, polymethylmethacrylate (PMMA), parylene-c, polyimide, polystyrene, bisdichlorosilylethane, bisdichlorosilylhexane, polyisobultylene, alumina, hafnium oxide and/or polyethylene. Although various dielectric materials can be suitable, typically the materials can have a dielectric constant greater than 3. The sensing and control gate electrodes can comprise at least one of the materials from the groups, heavily doped inorganic semiconductors, conductive polymers, graphene, conductive composites, metals, graphite, and ionic gels/liquids.

Figure 5:
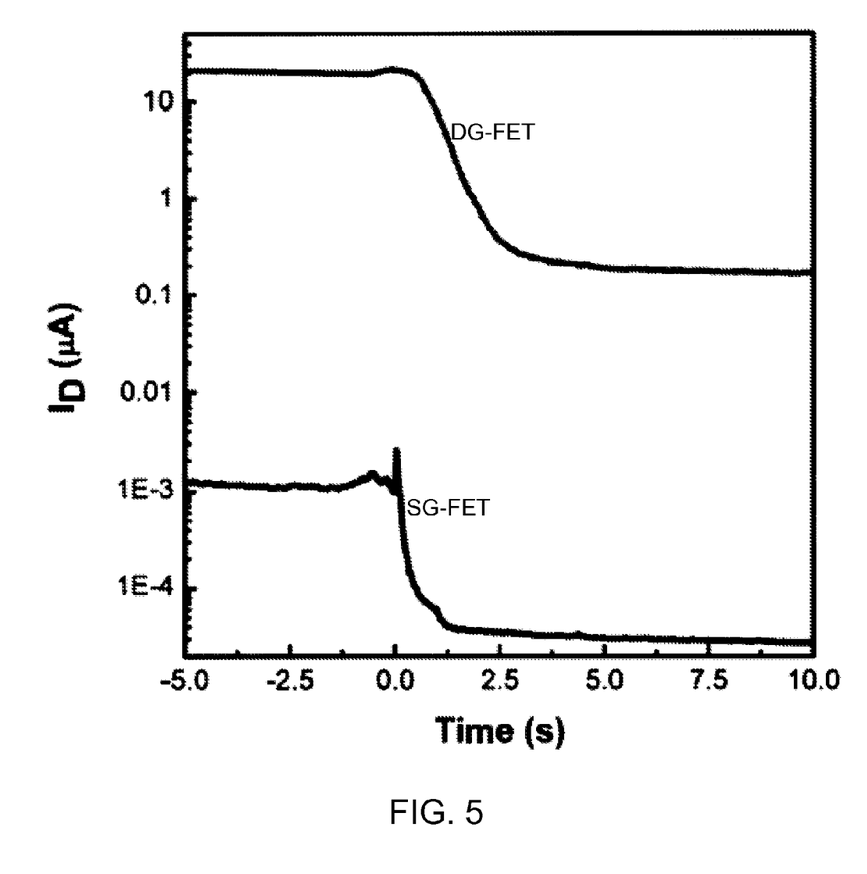
FIG. 5 is a comparison plot of drain current over time for a dual gate (DG) chemical-sensing field effect transistor (chemFET) versus a sensing gate (SG) chemFET when exposed to ammonia in accordance with one example of the present invention.

FIG. 5 is an exemplary comparison plot of drain current over time for a dual gate (DG) chemical-sensing field effect transistor (chemFET) versus a sensing gate (SG) chemFET. As shown in FIG. 5, the dual gate (DG) FET sensor provides a sensitivity advantage as compared to the single-gate sensing gate (SG) FET sensor. In one example, testing shows that the drain current signal for the DG FET sensor is 10,000 times greater than the drain current signal for the SG FET sensor.

Figure 6A:
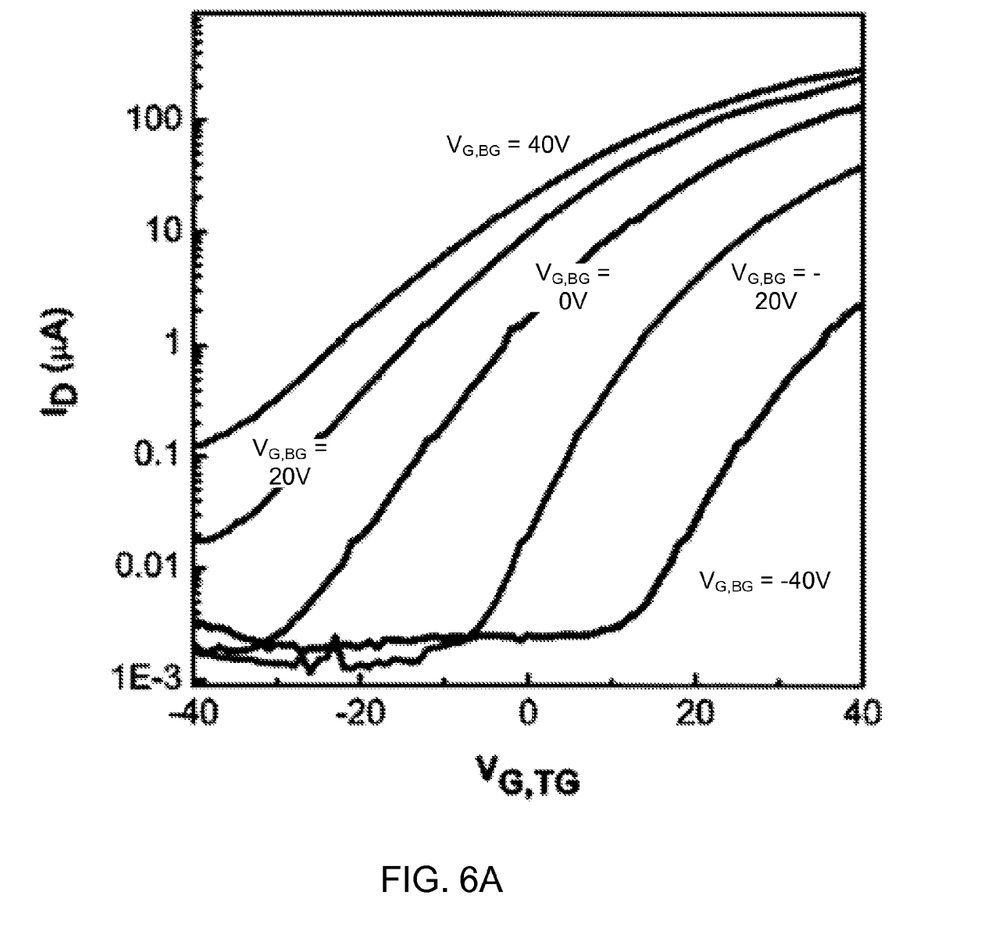
FIGS. 6A and 6B illustrate plots of drain current versus sensing gate voltage that indicates the modulation of a sensing gate threshold voltage by a control gate voltage for a dual gate (DG) chemical-sensing field effect transistor (chemFET) in accordance with one example of the present invention.
Figure 6B:
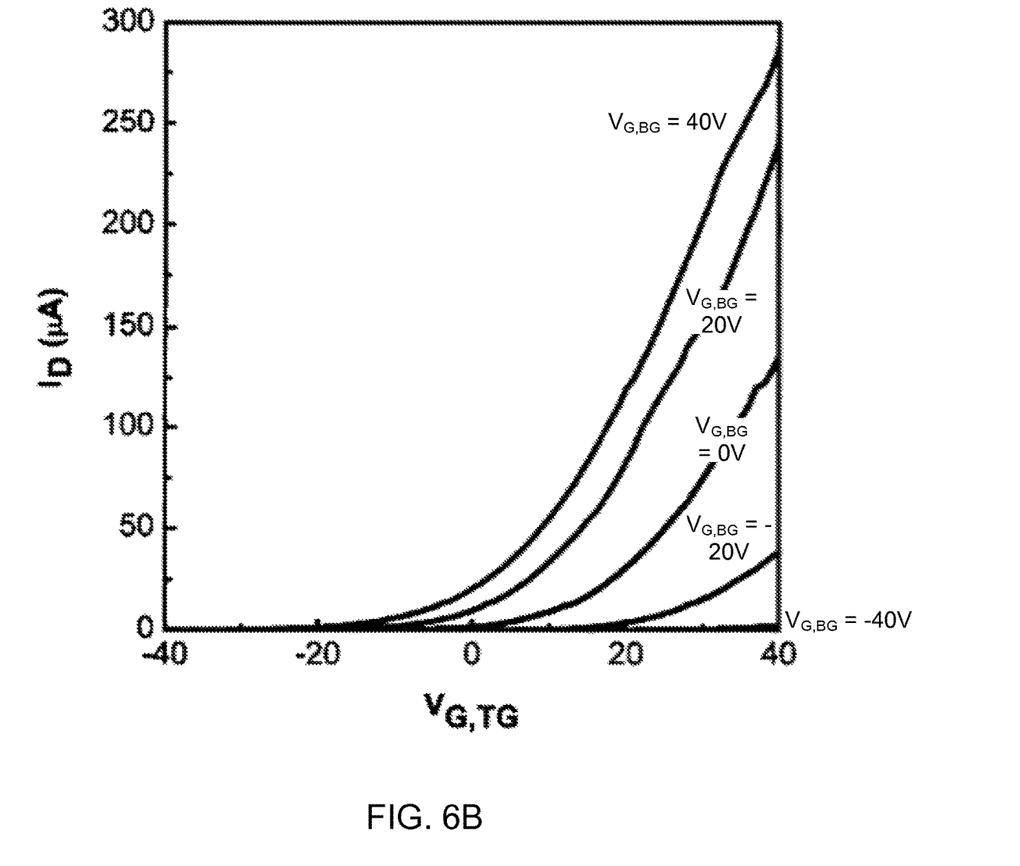

FIGS. 6A and 6B illustrate exemplary plots of drain current versus sensing gate voltage that indicates the modulation of a sensing gate threshold voltage by a control gate voltage for a dual gate (DG) chemical-sensing field effect transistor (chemFET). The plot of the drain current versus the sensing gate voltage can represent the performance of the DG chemFET showing how the control gate voltage modulates sensing gate threshold voltage and satisfies interface trap charges. Drain current gate voltage (IdVg) curves can be measured for the DG chemFET that illustrate how the threshold voltage is modulated by the control gate voltage. With respect to FIGS. 6A and 6B, "BG" refers to back gate, which is the control gate and "TG" refers to top gate, which is the sensing gate.

In FIG. 6A, where the drain current axis is in log format, the shift in the curve of each line represents an influence of trap charges on the drain current at that control gate bias. Thus, as the curve shifts to the left, more trap states are filled. The plot shows that, as control gate bias is increased, the IdVg curve also shifts, indicating a reduction in the influence of interface trap charges on drain current as control gate voltage is increased. In FIG. 6B, linear portions of the IdVg curve for each tested control gate bias voltage can be extrapolated to the Vg axis where intersection with the Vg axis represents an approximation of the threshold voltage. The plot shows a reduction in threshold voltage at the sensing gate from about 17V to 8.5V to 3V with control gate biases of 0V, 20V, and 40V respectively.

Figure 7:
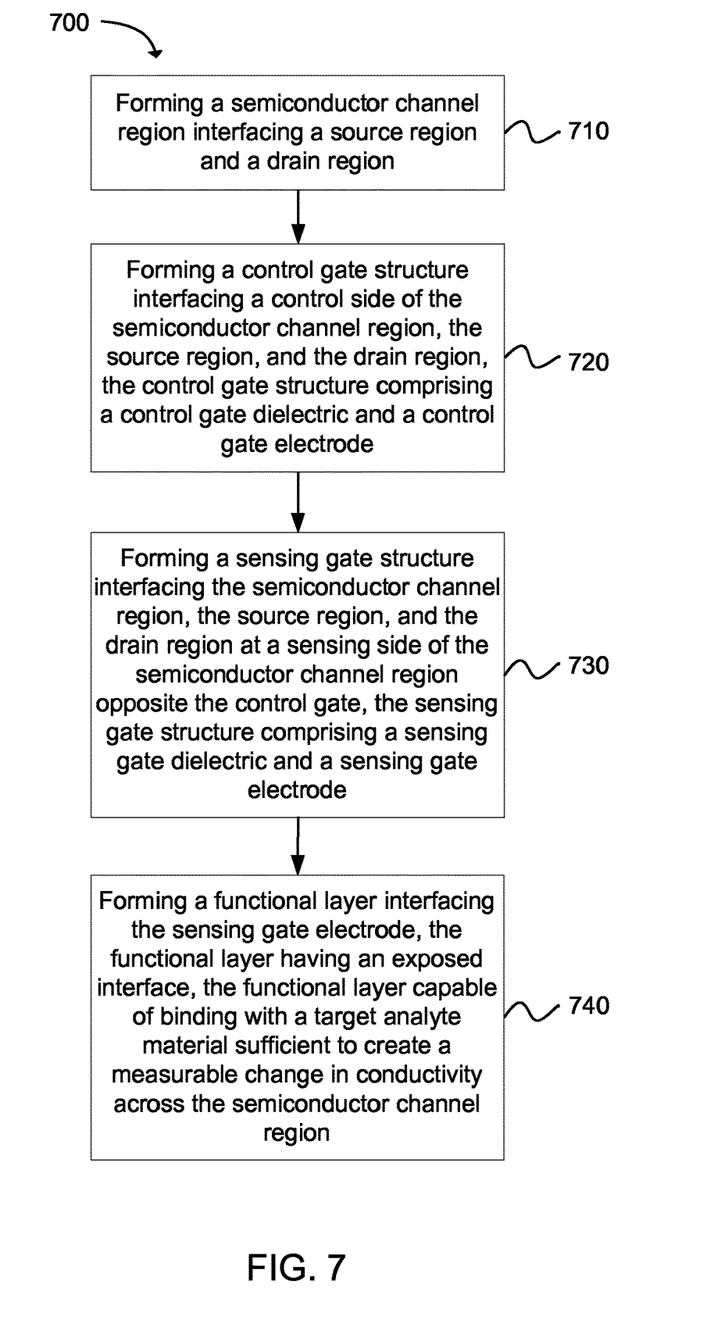
FIG. 7 is a flowchart of an example method for fabricating a chemical sensing field effect transistor device in accordance with one example of the present invention.

FIG. 7 is an exemplary flowchart of a method for fabricating a chemical sensing field effect transistor device. The method can include the operation of forming a semiconductor channel region interfacing a source region and a drain region, as in block 710. The method can also include the operation of forming a control gate structure interfacing a control side of the semiconductor channel region, the source region, and the drain region, the control gate structure comprising a control gate dielectric and a control gate electrode, as in block 720. The method can include the operation of forming a sensing gate structure interfacing the semiconductor channel region, the source region, and the drain region at a sensing side of the semiconductor channel region opposite the control gate, the sensing gate structure comprising a sensing gate dielectric and a sensing gate electrode, as in block 730. The method can include the operation of forming a functional layer interfacing the sensing gate electrode, the functional layer having an exposed interface, the functional layer capable of binding with a target analyte material sufficient to create a measurable change in conductivity across the semiconductor channel region, as in block 740.

In one configuration, the DG-FET can be easily modified to detect different chemical species. Detecting a new chemical can involve changing a functional layer (or functional material) of the DG-FET; the other components of the DG-FET remain the same. Due to the large number of different types of functional materials, the DG-FET can be used to detect a large number of different chemical species. Therefore, the DG-FET has increased flexibility in the materials that can be used as the sensing material. As a non-limiting example, the functional material can be a perylenetetracarboxylic diimide (PTCDI). The functional material can have the ability to transfer charges to or from the analyte. In traditional systems, the best selectivity has been from organic nanofiber chemiresistors. The major drawback in these systems is that the materials have to be electrically conductive. In the DG-FET, no conductivity is required such that the functional materials can optionally be non-conductive. As a result, this broadens the number of sensory materials that are available for use, which can lead to superior selectivity by using an array. Therefore, the large number of possible functional materials can eliminate the tradeoff between selectivity and conductivity that is often faced in chemiresistors. The DG-FET can enable selection of the functional material without the need for conductivity.

The DG-FET in the present technology provides several differences from the previous FETs used for chemical detection (i.e., the SS-FET and the SG-FET). First, the semiconducting materials generally used in SS-FETs and SG-FETs are generally different than the semiconducting materials used in the DG-FET. The SS-FETs typically uses small molecule organic semiconductors, such as pentacene. The SG-FETs typically uses inorganic semiconductors, such as silicon or indium zinc oxide (IZO), although organic semiconductors are also used. In contrast, the DG-FET can use organic polymers or certain types of inorganic semiconductors, such as indium zinc oxide (IZO). In addition, the small molecule organics used in SS-FETs are incompatible with SG-FETs and DG-FETs. Furthermore, surface roughness that is common for SS-FETs is detrimental to the performance of SG-FETs. Another difference between SS-FETs and SG-FETs is differences in the sensing mechanism between SS-FETs and SG-FETs. SS-FETs generally require that the analyte diffuse into the material, thereby creating barriers to current flow. In the SG-FETs and DG-FETs, the effect is charge transfer. Furthermore, theoretical calculations show that the two gates in the DG-FET (i.e., the sensing gate and the control gate) should not be able to communicate with each other due to the thickness of the semiconductor, which should screen the charges at the interface. However, experimental results show that the semiconductor can be up to approximately 20 nanometers (nm) without losing communication between the two gates in the DG-FET (i.e., the sensing gate and the control gate). Thus, in one aspect, the semiconductor thickness can be from 5 nm to 30 nm, in some cases from 14 nm to 25 nm, and in other cases from 18 nm to 22 nm.

As previously described, in SS-FETs, an organic semiconductor is exposed to the environment. An electric field is used to induce a current in an otherwise insulating materials. SS-FETs produce excellent sensitivity, into the parts per trillion range. However, SS-FETs produce poor selectivity. SS-FETs are triggered by a variety of mechanisms, instead of being limited to charge transfer, which can lead to relatively high false positive rates with common interferents, such as humid air. In SG-FETs, encapsulates the semiconductor layer and exposes the gate electrode to the environment. With the semiconductor layer encapsulated, the triggering mechanisms are limited to charge transfer, which greatly improves selectivity. In addition, organic materials can be placed on the gate electrode to further enhance selectivity. The main advantage of SG-FETs, in comparison to SS-FETs, is decoupling of the requirement for a material to be both sensitive and conductive. In SG-FETs, separate materials can work together to satisfy the sensitivity and conductivity needs. This allows for a wide variety of sensing materials (e.g., organic materials) to be used, enabling the SG-FET to be tailored to a wide number of applications. However, the SG-FET does not have an electric field to enable the flow of current, which results in the SG-FET having poor sensitivity.

In the present technology, the novel DG-FET can overcome the disadvantages of the SS-FET and the SG-FET. In the DG-FET, the semiconductor can be sandwiched between two gate electrodes. In particular, the semiconductor can be sandwiched between a sensing gate and a control gate. A sensing gate dielectric can be in between the sensing gate and the semiconductor, and a control gate dielectric can be in between the control gate and the semiconductor. The control gate can induce conductivity in the semiconductor by applying an electric field. The DG-FET combines the high sensitivity of the SS-FET with the excellent selectivity of the SG-FET. In addition, the processes used to fabricate DG-FETs are standard in waferscale semiconductor production, which can result in reduced costs. The DG-FET is an inexpensive device that can be tailored to a large number of chemical detection applications. Sensing systems built around DG-FETs have the potential to improve human health, food safety, national security, etc.

In one configuration, the sensitivity of the DG-FET can be enhanced using several techniques. In a first technique, the semiconductor layer can be substituted by a material with increased charge carrier mobility, as this will enhance the signal. The semiconductor layer can also be thinned, which can improve communication between the sensing gate and the control gate in the DG-FET. In a second technique, a capacitance of the dielectric layers (i.e., the sensing gate dielectric and the control gate dielectric) can be increased. In previous solutions, the capacitance of the dielectrics (or films) used is fairly low, which can introduce significant losses in the signal as it is transmitted from the gate to the semiconductor. Using a thinner film with a higher dielectric constant (e.g., $Al_2O_3$, $HfO_2$) can increase the capacitance and eliminate the losses. In a third technique, the use of nanostructures on the gate electrode can increase surface area, which can lead to a larger interface with the analyte. The larger interface can increase the likelihood of catching a molecule of interest, and thereby, can result in improved sensitivity.

In one configuration, the selectivity of the DG-FET can be improved by functionalizing the sensing gate electrode. The functional material can be responsible for interacting with the chemical species. The functional material can be designed to capture chemical species of interest while blocking potential interferents. Selectivity can be further improved by creating an array of sensors. Even though different functional materials can allow responses to a class of chemical species (e.g., amines), each response can be unique. Using an array generates a specific fingerprint for each chemical species, which can enable for the determination of the presence of a specific chemical.

In one configuration, fabrication of the DG-FET can use existing fabrication methodologies, thereby enabling low-cost production. In one example, a degenerately doped silicon substrate forms the control gate electrode and processing follows a bottom-to-top route wherein the control gate electrode represents the bottom of the device over which a planar DG-FET is fabricated. Thermal oxidation of this substrate grows a silicon dioxide dielectric which serves as the control gate dielectric layer. Alternatively, the control gate dielectric can be formed via solution-processed deposition, chemical vapor deposition, or physical vapor deposition and comprises at least one member of the group consisting of polymethylmethacrylate (PMMA), parylene-c, polyimide, polystyrene, bisdichlorosilylethane, bisdichlorosilylhexane and polyisobultylene, silicon nitride, silicon oxynitride, alumina, and hafnium oxide. An organic semiconductor, such as a conducting polymer (e.g., polythiophene, polynaphthalene), can be deposited on top of the control gate dielectric to form the semiconductor channel as well as the regions that will function as the source and drain of the FET. This can be done through any one of the processes: solution-processed deposition, electropolymerization, vacuum evaporation and, less commonly, the Langmuir Blodgett technique. Other organic semiconductors such as polythiophenes, oligothiophenes, phalocyanines, pentacene, benzodithiophene, carbonyl-bridged bithiazole, and alkyl substituted dioxocyclopenta[b]thiophene as well as hybrid graphene/organic, hybrid carbon nanotubes/organic, and hybrid inorganic/organic semiconductors can also be used to form the semiconductor channel layer. Once the organic semiconductor layer is deposited, the control gate dielectric is oriented between the control gate electrode and the semiconductor channel. Source and drain regions can be native or optionally be formed from selected regions of the organic semiconductor layer by one of the oxidation-reduction processes: chemical doping and electrochemical doping. Typically, the electrodes can be deposited and then semiconductor material is deposited subsequently although other approaches can be suitable.

In alternative embodiments, source and drain regions are not formed from the organic semiconductor material, but are ink-jet printed using liquid precursors to conductive materials to be subsequently sintered to form conductive interfaces with the organic semiconductor channel. In another alternative, source and drain regions can be formed by sputtering gold on a photoresist mask patterned using photolithography. After formation of the semiconductor channel, source, and drain, a sensing gate dielectric layer can be deposited. This can be done through solution-based deposition, a low temperature process that does not approach the thermal budget of the organic semiconductor beyond which critical functional properties are degraded. Non-limiting examples of potential dielectric materials that can be deposited through solution-based deposition are silicon dioxide, polymethylmethacrylate (PMMA), parylene-c, polyimide, polystyrene, bisdichlorosilylethane, bisdichlorosilylhexane and polyisobultylene.

The sensing gate electrode can then be deposited onto the sensing gate dielectric so that the sensing gate dielectric is oriented between the semiconductor channel and the sensing gate electrode. This can be done through any one of the following processes: evaporation, vacuum deposition, chemical vapor deposition, atomic layer deposition, physical vapor deposition, and inkjet printing. Sensing gate conductors formed from these processes can include conductive polymers, conductive composites, metals, metal compounds, and ionic gels/liquids. Another embodiment can include graphene as a sensing gate electrode requiring a transfer of a graphene layer from a different substrate to the sensing gate dielectric layer of the developing DG-FET.

The functional layer can be deposited onto the sensing gate electrode. Suitable functional layer materials can include, but are not limited to, perylene imides, porphyrins, phthalocyanines, carbazoles, anilines, thiophenes, pyrroles, and ketones. Processes through which the functional layer can be formed can include physical vapor deposition, chemical vapor deposition, and solution-based deposition, although other processes may be suitable. The functional layer material can be chosen according to its adsorptive interaction with a target analyte material. Several exemplary combinations of functional layer and analyte binding moieties are listed in Table 1.

TABLE 1

Functional Materials, Target Analytes, and Applications

| Functional Layer Molecule Class | Target Analyte Species | Applications |
| --- | --- | --- |
| Perylene imides | Amines, nitros, peroxides, CWAs | Narcotics, explosives, medical, building health, air quality, defense |
| Porphyrins and phthalocyanines | Peroxides, cyanides, nitros, toxic gases | Explosives, building health, air quality, explosives, health and safety |
| Carbazoles | Nitros | Explosives, air quality |
| Anilines | Amines, aldehydes, acids, other VOCs | Narcotics, medical, building health, health and safety, air quality |
| Thiophenes | Acids, cyanides, nitros, CWAs, other VOCs | Health and safety, air quality, explosives, defense, building health |
| Pyrroles | Acids, amines, toxic gases, other VOCs | Health and safety, narcotics, health, building health, air quality |
| Ketones | Amines, Acids | Health and safety |

This functional layer can be from 1 nm to 10 µm in thickness and can be formed with a micro-structured or a nano-structured surface to morphologically facilitate target analyte adsorption (e.g. nanofibers, pyramids, pillars, etc).

Such structured surfaces can be formed, for example, by chemical vapor deposition, physical vapor deposition, electroplating, etching (wet and dry), embossing, nanoimprint lithography, self-assembly, although other methods can be used.

In the above described DG-FET, the processing results in a lamellar structure and the channel is designed to direct current flow parallel to the lamellae. If the exposed surface of the functional layer is smooth, it can have a surface area equal to the lamellae beneath it, which is equivalent to the entire area of the bottom-most layer, the control gate electrode. Because the source and drain regions occupy space within the same plane as the channel region, the surface area of a smooth exposed functional layer is substantially greater than the interface area between the channel and the sensing gate electrode. If the exposed surface of the functional layer is microstructured or nanostructured the difference between exposed functional layer surface area and the interface area between channel and sensing gate dielectric is greater still.

Another embodiment wherein a DG-FET is formed starting with a heavily doped silicon substrate and progressing along a bottom-to-top process route can result in a repeated trench structure with a channel designed to direct current flow substantially orthogonal to the plane of the exposed functional layer. In this embodiment, the heavily doped silicon substrate serves as the drain rather than the control gate electrode. The organic semiconductor can be deposited via solution-based processing, and source region stripes can be defined and formed by masked chemical doping, electrochemical doping, or inkjet printing of conductive materials. Non-conductive areas can be etched to form trenches in the semiconductor layer end-pointing at the heavily doped silicon drain layer such that the drain is exposed at the bottom of the trenches. A solution-based deposition of an insulator layer nearly fills the trenches, leaving a thin dielectric film over the mesas. An etch-back removes the film from the mesas and removes some of the dielectric from the trench centers, but leaves a substantial layer of dielectric on the sides and bottom of each trench. These dielectric troughs serve as the dielectric regions of the sensing and control gates. At this point, trenches are identical and electrically isolated from each other. Subsequent process steps distinguish sensing and control gate structures in alternating trenches. Deposition of a layer of conductive material followed by an etch over the control gate trench edges as well as other areas defining a source contact pad, control gate electrode pad, and respective lead lines restores electrical isolation between the sensing gate and control gate electrodes.

One last solution-processed deposition of dielectric substantially planarizes the device surface, capping the control gate structure and insulating it electrically from the sensing gate electrodes. An etch step exposes the sensing gate electrode material. Finally, the functional layer is deposited over the entire device front surface, then selectively removed to expose source and gate pad contact areas. The back side of the heavily doped silicon substrate is thinned, then coated with a conductive material for contact with the device's support circuitry. Lined trenches comprise the sensing gate and control gate structures that interface the organic semiconductor channel between them. Because the drain region lies at the bottom of the device, and the source region at the top of the mesas between trenches, current is channeled orthogonal to the plane of the functional layer. This vertical channel design potentially shortens the distance between source and drain while maintaining the high surface area of the functional layer, thereby further mitigating challenges with organic semiconductor mobility. Therefore, this embodiment also produces a DG-FET device with an exposed functional surface area substantially greater than the surface area of the interface between the channel and the sensing gate dielectric.

Yet another embodiment wherein a DG-FET is formed includes an inorganic semiconductor channel material. In this case, the process route need not be strictly bottom-to-top. The inorganic semiconductor material comprises one or more semiconductor materials categorized by the periodic table of elements as group IV, III-V, II-VI, I-VI$_2$, or I$_2$-II-IV-VI$_4$ and are optionally doped with one or more charge donors and acceptors. In one aspect of this embodiment, a starting material substrate can comprise a single crystalline silicon wafer with a buried oxide layer. The device can be built in substantially planar layers to result in a channel that directs current parallel to the substrate and the exposed functional material surfaces. The channel, drain, source, and control gate structures are formed first. Selective implantation of acceptor or donor dopants forms the source and drain regions interfacing the channel region and lying within the same plane. The silicon substrate undergoes thermal oxidation, then metal deposition to form the control gate dielectric and electrode. The substrate is flipped, and thinned, then etched back to the buried oxide layer that serves as the sensing gate dielectric. Metal is then deposited over the oxide to form the sensing gate electrode. A functional layer is deposited over the sensing gate electrode to complete an inorganic-channel DG-FET structure similar in function and dimensions to the preceding description of a lamellar organic-channel DG-FET. Similar to the organic-channel DG-FET design, the exposed functional layer surface area of this inorganic-channel DG-FET is substantially greater than the interface area between the channel and the sensing gate dielectric.

The above-described embodiments explain how the DG-FET combines the advantageous selectivity and wide range of functional materials of the SG-FET with the high sensitivity of the SS-FET. The addition of the second gate will enable the first practical applications for chemFETs.

Practical Applications

With a virtually unlimited number of functional materials there are essentially endless possibilities for DG-FET commercialization. Examples of potential applications are described below.

Sick building syndrome is increasingly problematic. It is caused by a buildup of pollutants that can be harmful in sufficient concentrations. The buildup is caused by two issues. First, the push for energy efficiency has led to better insulated buildings. In fact, ventilation rates have dropped by 80% over the past 50 years. Increasing population density is another contributing factor, with more people performing more polluting activities in a given building. Hazardous chemicals produced through indoor activities include carbon dioxide, carbon monoxide, formaldehyde, nitrogen dioxide, and various organic materials. At present, there is no system available for monitoring a wide variety of chemical species. DG-FET sensors can be designed for each species of interest and operate in a low cost array in every room in a building. This system can be tied to the ventilation system to provide feedback on when more fresh air is needed. Such a system balances the need for energy efficiency with the requirement that hazardous chemicals be exhausted.

Air pollution is a perpetually growing concern. As cities modernize, air polluting industries and activities increase, as in the case of Beijing. While particle counters are widely used to monitor soot in the air, there is essentially no technology in use to characterize toxic chemical species. Nitrogen dioxide, carbon monoxide, and hydrogen cyanide (HCN) are all examples of toxic gases produced during combustion, with HCN lethal at just 50 parts per million. There is tremendous potential here for an inexpensive sensor for air quality monitoring. Two potential implementations exist. Governments could install monitoring stations throughout regions of interest to better predict potential health risks. Cheap, handheld systems can also be sold to individual consumers, and optionally as attachments to smart phones. In this manner, a person can evaluate the quality of air in their local environment.

Additional applications can be found in the medical diagnostic business. While volatile organic compounds are always present in a person's breath, certain concentrations are indicative of certain diseases, e.g. as biomarkers. Diabetics, for example, have an elevated level of acetone in their breath. Detection remains difficult for current technologies because of a strict resolution requirement. The control gate of the DG-FET can meet this resolution because it offers a mechanism to overcome variation between devices. The control voltage can be adjusted to set the sensor at exactly the same set point for each test, regardless of manufacturing variability. In addition to diagnostics, breath can also be used to monitor blood sugar, eliminating the need for blood tests. The DG-FET has the potential to provide cheap, instantaneous, noninvasive testing for diabetes and other disorders, including asthma, chronic obstructive pulmonary disease, angina, cystic fibrosis, and certain cancers.

Monitoring food supplies is another area that can benefit from chemical detection. When foods spoil, they release ethylene oxide. Ethylene oxide also causes spoilage in foods. Monitoring ethylene oxide concentrations can alert a user that a food is about to go bad so that it can be removed before it has the opportunity to spoil other foods. This could reduce losses in grocery stores, warehouses, and kitchens.

There are opportunities in the aerospace industry as well. This research is sponsored by NASA. Cabin air quality on extended manned missions is a critical issue. There is no means of obtaining fresh air in space, so it is all recycled. Air scrubbers are imperfect and occasionally break, creating a life threatening scenario. Currently, air quality is monitored by MS, which is bulky and expensive. A small, low-cost, low power alternative is appealing.

This same technology could be used on commercial aircraft and submarines. Aside from air quality, there are applications in leak detection. The Air Force recently solicited proposals to put sensors in the wings of its aircraft to detect leaks in the fuel system. There are many volatile components in jet fuel that would be possible to detect using the DG-FET.

Finally, there are potential applications in the defense industry. The Department of Defense has expressed a strong desire to improve its ability to detect chemical weapons near soldiers. Ideally, each soldier would have a person detector. Current approaches are too expensive, but the DG-FET has the potential to be implemented as a low cost, personal sensor for chemical weapons.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A dual gate (DG) chemical sensing field effect transistor (chemFET) device operable to perform airborne chemical detection, the DG chemFET device comprising:
- a sensing gate electrode;
- a control gate electrode;
- an organic semiconductor layer positioned in between the sensing gate electrode and the control gate electrode, wherein a sensing gate dielectric separates the organic semiconductor layer from the sensing gate electrode and a control gate dielectric separates the organic semiconductor layer from the control gate electrode, wherein conductivity is induced in the organic semiconductor by application of an electric field by the control gate electrode; and
- a sensing material placed on the sensing gate electrode to enable detection of airborne chemicals, wherein the sensing material is selected based on a type of airborne chemical to be detected using the DG chemFET,
- wherein the DG chemFET is operable to perform airborne chemical detection with increased selectivity and increased sensitivity based in part on the sensing gate electrode that is opposite of the control gate electrode with respect to the organic semiconductor layer.

2. The device of claim 1, wherein the control gate dielectric is oriented between the organic semiconductor layer and the control gate electrode.

3. The device of claim 1, wherein the sensing gate dielectric is oriented between the organic semiconductor layer and the sensing gate electrode.

4. The device of claim 1, wherein the organic semiconductor layer comprises at least one of: polythiophenes, polynaphthalyene, polyphenylenevinylene, parylenediimides, oligothiophenes, phalocyanines, pentacene, benzodithiophene, carbonyl-bridged bithiazole, and alkyl substituted dioxocyclopenta[b]thiophene.

5. The device of claim 1, wherein the organic semiconductor layer further comprises a graphene to form a hybrid graphene/organic semiconductor.

6. The device of claim 1, wherein a surface area of the sensing material is substantially greater than an interface area between the organic semiconductor layer and the sensing gate dielectric.

7. The device of claim 1, further comprising a drain region and a source region oriented at an interface of the sensing gate dielectric, the control gate dielectric, and the organic semiconductor layer.

8. The device of claim 1, wherein a flow of current through the organic semiconductor layer is substantially parallel to a plane of the sensing material.

9. The device of claim 1, wherein a flow of current through the organic semiconductor layer is substantially orthogonal to a plane of the sensing material.

10. The device of claim 1, wherein the sensing gate dielectric and the control gate dielectric comprise at least one of: silicon dioxide, polymethylmethacrylate (PMMA), parylene-c, polyimide, polystyrene, bisdichlorosilylethane, bisdichlorosilylhexane, polyisobultylene, alumina, and hafnium oxide.

11. The device of claim 1, wherein the sensing gate electrode and the control gate electrode comprise at least one of: heavily doped inorganic semiconductors, conductive polymers, graphene, conductive composites, metals, ionic gels/liquids, and combinations thereof.

12. The device of claim 1, wherein the sensing material comprises at least one member selected from the group consisting of: perylene imides, porphyrins and phthalocyanines, carbazoles, anilines, thiophenes, pyrroles, ketones, carbon nanotubes, metal oxides and combinations thereof, the sensing material being chosen according to a level of adsorptive interaction with a target analyte material sufficient to create a measurable change in conductivity across the organic semiconductor layer.

13. The device of claim 1, wherein the sensing material is a functional layer from 1 nanometer (nm) to 10 micrometers (μm) in thickness.

14. The device of claim 1, wherein the functional layer includes a micro-structured or a nano-structured surface to morphologically facilitate target analyte adsorption.

15. The device of claim 1, wherein the sensing material is not conductive.

16. The device of claim 1, wherein the sensing material is exposed to atmosphere.

* * * * *